(12) United States Patent
Ushio et al.

(10) Patent No.: US 6,214,584 B1
(45) Date of Patent: Apr. 10, 2001

(54) HUMAN INTERFERON-γ INDUCING FACTOR

(75) Inventors: Shimpei Ushio; Kakuji Torigoe; Tadao Tanimoto, all of Okayama; Haruki Okamura, Osaka; Masashi Kurimoto, Okayama, all of (JP)

(73) Assignee: Kabushiki Kaisha Hayashibara Seibutsu Kagaku Kenkyujo, Okayama (JP)

( * ) Notice: Subject to any disclaimer, the term of this patent is extended or adjusted under 35 U.S.C. 154(b) by 0 days.

(21) Appl. No.: 08/832,180

(22) Filed: Apr. 8, 1997

Related U.S. Application Data

(62) Division of application No. 08/558,191, filed on Nov. 15, 1995.

(30) Foreign Application Priority Data

Nov. 15, 1994 (JP) .................................... 6-304203
Sep. 18, 1995 (JP) .................................... 7-262062

(51) Int. Cl.$^7$ .......................... C12P 21/06; C12N 15/00; C12N 15/09; C12N 15/63
(52) U.S. Cl. .................... 435/69.52; 435/320.1; 435/325; 435/69.1; 435/69.5; 435/252.3; 435/252.33; 530/324; 530/351; 536/23.51
(58) Field of Search ........................ 536/23.51; 435/69.1, 435/61.5, 65.52, 325, 320.1, 252.3, 252.33; 530/324, 351

(56) References Cited

FOREIGN PATENT DOCUMENTS 0692536   1/1996  (EP) .
9205256   4/1992  (WO) .
97/24441 * 7/1997  (WO) .

OTHER PUBLICATIONS

Okamura et al., "Cloning of a new cytokine that induces IFN– production by T cells", *Letters To Nature* vol. 378, pp. 88–91, (1995).

XP–002024314, (1993).

Japan Abstract 05279376, Oct. 26, 1993.

H. Okamura et al, "Cloning of a new cytokine that induce IFN–gamma production by T cells", Nature, vol. 378, No. 6552, pp. 88–92.

Sambrook, J. et al., "Molecular Cloning, A Laboratory Manual." 2nd Edition, pp. xi–xxxviii (1989).

Muramatsu, Masami., "Laboratory Manual for Genetic Engineering." pp. v–ix, (1988).

* cited by examiner

*Primary Examiner*—David L. Fitzgerald
*Assistant Examiner*—Janet L. Andres
(74) *Attorney, Agent, or Firm*—Browdy And Neimark

(57) ABSTRACT

A polypeptide which has a molecular weight of 18,500±3,000 daltons on SDS-PAGE and a pI of 4.9±1.0 on chromatofocusing. The polypeptide strongly induces the IFN-γ production by immunocompetent cells with only a small amount, and does not cause serious side effects even when administered to human in a relatively-high dose. It can be used to treat and/or prevent malignant tumors, viral diseases, bacterial infectious diseases, and immune diseases.

31 Claims, 2 Drawing Sheets

SEQUENCE LISTING (1) GENERAL INFORMATION:

(iii) NUMBER OF SEQUENCES:14

(2) INFORMATION FOR SEQ ID NO:1:

(i) SEQUENCE CHARACTERISTICS:
        (A) LENGTH:157 amino acids
        (B) TYPE:amino acid
        (C) STRANDEDNESS:single
        (D) TOPOLOGY:linear (ii) MOLECULE TYPE:peptide (xi) SEQUENCE DESCRIPTION:SEQ ID NO:1:

Tyr Phe Gly Lys Leu Glu Ser Lys Leu Ser Val Ile Arg Asn Leu Asn
1             5                   10                15

Asp Gln Val Leu Phe Ile Asp Gln Gly Asn Arg Pro Leu Phe Glu Asp

```
                    20                  25                  30
Met Thr Asp Ser Asp Cys Arg Asp Asn Ala Pro Arg Thr Ile Phe Ile
                35                  40                  45

Ile Ser Met Tyr Lys Asp Ser Gln Pro Arg Gly Met Ala Val Thr Ile
     50                  55                  60

Ser Val Lys Cys Glu Lys Ile Ser Xaa Leu Ser Cys Glu Asn Lys Ile
 65                  70                  75                  80

Ile Ser Phe Lys Glu Met Asn Pro Pro Asp Asn Ile Lys Asp Thr Lys
                 85                  90                  95

Ser Asp Ile Ile Phe Phe Gln Arg Ser Val Pro Gly His Asp Asn Lys
                100                 105                 110

Met Gln Phe Glu Ser Ser Ser Tyr Glu Gly Tyr Phe Leu Ala Cys Glu
            115                 120                 125

Lys Glu Arg Asp Leu Phe Lys Leu Ile Leu Lys Lys Glu Asp Glu Leu
        130                 135                 140

Gly Asp Arg Ser Ile Met Phe Thr Val Gln Asn Glu Asp
145                 150                 155
```

(2) INFORMATION FOR SEQ ID NO:2:

(i) SEQUENCE CHARACTERISTICS:
        (A) LENGTH:471 base pairs
        (B) TYPE:nucleic acid
        (C) STRANDEDNESS:single
        (D) TOPOLOGY:linear (xi) SEQUENCE DESCRIPTION:SEQ ID NO:2:

```
TACTTTGGCA AGCTTGAATC TAAATTATCA GTCATAAGAA ATTTGAATGA CCAAGTTCTC      60

TTCATTGACC AAGGAAATCG GCCTCTATTT GAAGATATGA CTGATTCTGA CTGTAGAGAT     120

AATGCACCCC GGACCATATT TATTATAAGT ATGTATAAAG ATAGCCAGCC TAGAGGTATG     180

GCTGTAACTA TCTCTGTGAA GTGTGAGAAA ATTTCAAYTC TCTCCTGTGA GAACAAAATT     240

ATTTCCTTTA AGGAAATGAA TCCTCCTGAT AACATCAAGG ATACAAAAAG TGACATCATA     300

TTCTTTCAGA GAAGTGTCCC AGGACATGAT AATAAGATGC AATTTGAATC TTCATCATAC     360

GAAGGATACT TTCTAGCTTG TGAAAAAGAG AGAGACCTTT TTAAACTCAT TTTGAAAAAA     420

GAGGATGAAT TGGGGGATAG ATCTATAATG TTCACTGTTC AAAACGAAGA C              471
```

(2) INFORMATION FOR SEQ ID NO:3:

(i) SEQUENCE CHARACTERISTICS:
        (A) LENGTH:471 base pairs
        (B) TYPE:nucleic acid
        (C) STRANDEDNESS:double
        (D) TOPOLOGY:linear (ii) MOLECULE TYPE:cDNA to mRNA (iii) HYPOTHETICAL:No (iv) ANTI-SENSE:No (vi) ORIGINAL SOURCE:
        (A) ORGANISM:mouse
        (F) TISSUE TYPE:liver (ix) FEATURE:
        (A) NAME/KEY:1-471 mat peptide
        (C) IDENTIFICATION METHOD:S (xi) SEQUENCE DESCRIPTION:SEQ ID NO:3:

```
AAC TTT GGC CGA CTT CAC TGT ACA ACC GCA GTA ATA CGG AAT ATA AAT       48
```

```
Asn Phe Gly Arg Leu His Cys Thr Thr Ala Val Ile Arg Asn Ile Asn
1               5                   10                  15

GAC CAA GTT CTC TTC GTT GAC AAA AGA CAG CCT GTG TTC GAG GAT ATG        96
Asp Gln Val Leu Phe Val Asp Lys Arg Gln Pro Val Phe Glu Asp Met
            20                  25                  30

ACT GAT ATT GAT CAA AGT GCC AGT GAA CCC CAG ACC AGA CTG ATA ATA       144
Thr Asp Ile Asp Gln Ser Ala Ser Glu Pro Gln Thr Arg Leu Ile Ile
        35                  40                  45

TAC ATG TAC AAA GAC AGT GAA GTA AGA GGA CTG GCT GTG ACC CTC TCT       192
Tyr Met Tyr Lys Asp Ser Glu Val Arg Gly Leu Ala Val Thr Leu Ser
    50                  55                  60

GTG AAG GAT AGT AAA AYG TCT ACC CTC TCC TGT AAG AAC AAG ATC ATT       240
Val Lys Asp Ser Lys Xaa Ser Thr Leu Ser Cys Lys Asn Lys Ile Ile
65                  70                  75                  80

TCC TTT GAG GAA ATG GAT CCA CCT GAA AAT ATT GAT GAT ATA CAA AGT       288
Ser Phe Glu Glu Met Asp Pro Pro Glu Asn Ile Asp Asp Ile Gln Ser
                85                  90                  95

GAT CTC ATA TTC TTT CAG AAA CGT GTT CCA GGA CAC AAC AAG ATG GAG       336
Asp Leu Ile Phe Phe Gln Lys Arg Val Pro Gly His Asn Lys Met Glu
            100                 105                 110

TTT GAA TCT TCA CTG TAT GAA GGA CAC TTT CTT GCT TGC CAA AAG GAA       384
Phe Glu Ser Ser Leu Tyr Glu Gly His Phe Leu Ala Cys Gln Lys Glu
        115                 120                 125

GAT GAT GCT TTC AAA CTC ATT CTG AAA AAA AAG GAT GAA AAT GGG GAT       432
Asp Asp Ala Phe Lys Leu Ile Leu Lys Lys Lys Asp Glu Asn Gly Asp
    130                 135                 140

AAA TCT GTA ATG TTC ACT CTC ACT AAC TTA CAT CAA AGT                   471
Lys Ser Val Met Phe Thr Leu Thr Asn Leu His Gln Ser
145                 150                 155

(2) INFORMATION FOR SEQ ID NO:4:

(i) SEQUENCE CHARACTERISTICS:
        (A) LENGTH:25 amino acids
        (B) TYPE:amino acid
        (C) STRANDEDNESS:single
        (D) TOPOLOGY:linear (ii) MOLECULE TYPE:peptide (v) FRAGMENT TYPE:internal fragment (xi) SEQUENCE DESCRIPTION:SEQ ID NO:4:

Ile Ile Ser Phe Glu Glu Met Asp Pro Pro Glu Asn Ile Asp Asp Ile
1               5                   10                  15

Gln Ser Asp Leu Ile Phe Phe Gln Lys
            20                  25

(2) INFORMATION FOR SEQ ID NO:5:

(i) SEQUENCE CHARACTERISTICS:
        (A) LENGTH:18 amino acids
        (B) TYPE:amino acid
        (C) STRANDEDNESS:single
        (D) TOPOLOGY:linear (ii) MOLECULE TYPE:peptide (v) FRAGMENT TYPE:internal fragment (xi) SEQUENCE DESCRIPTION:SEQ ID NO:5:

Gln Pro Val Phe Glu Asp Met Thr Asp Ile Asp Gln Ser Ala Ser Glu
1               5                   10                  15

Pro Gln
```

(2) INFORMATION FOR SEQ ID NO:6:

(i) SEQUENCE CHARACTERISTICS:
        (A) LENGTH:1120 base pairs
        (B) TYPE:nucleic acid
        (C) STRANDEDNESS:double
        (D) TOPOLOGY:linear (ii) MOLECULE TYPE:cDNA to mRNA (iii) HYPOTHETICAL:No (iv) ANTI-SENSE:No (vi) ORIGINAL SOURCE:
        (A) ORGANISM:human
        (F) TISSUE TYPE:liver (ix) FEATURE:
        (A) NAME/KEY:1-177 5'-UTR
        (C) IDENTIFICATION METHOD:S (ix) FEATURE:
        (A) NAME/KEY:178-285 leader peptide
        (C) IDENTIFICATION METHOD:S (ix) FEATURE:
        (A) NAME/KEY:286-756 mat peptide
        (C) IDENTIFICATION METHOD:S (ix) FEATURE:
        (A) NAME/KEY:757-1120 3'-UTR
        (C) IDENTIFICATION METHOD:S (xi) SEQUENCE DESCRIPTION:SEQ ID NO:6:

```
GCCTGGACAG TCAGCAAGGA ATTGTCTCCC AGTGCATTTT GCCCTCCTGG CTGCCAACTC        60

TGGCTGCTAA AGCGGCTGCC ACCTGCTGCA GTCTACACAG CTTCGGGAAG AGGAAAGGAA       120

CCTCAGACCT TCCAGATCGC TTCCTCTCGC AACAAACTAT TTGTCGCAGG AATAAAG          177

ATG GCT GCT GAA CCA GTA GAA GAC AAT TGC ATC AAC TTT GTG GCA ATG         225
Met Ala Ala Glu Pro Val Glu Asp Asn Cys Ile Asn Phe Val Ala Met
1               5                   10                  15

AAA TTT ATT GAC AAT ACG CTT TAC TTT ATA GCT GAA GAT GAT GAA AAC         273
Lys Phe Ile Asp Asn Thr Leu Tyr Phe Ile Ala Glu Asp Asp Glu Asn
                20                  25                  30

CTG GAA TCA GAT TAC TTT GGC AAG CTT GAA TCT AAA TTA TCA GTC ATA         321
Leu Glu Ser Asp Tyr Phe Gly Lys Leu Glu Ser Lys Leu Ser Val Ile
            35                  40                  45

AGA AAT TTG AAT GAC CAA GTT CTC TTC ATT GAC CAA GGA AAT CGG CCT         369
Arg Asn Leu Asn Asp Gln Val Leu Phe Ile Asp Gln Gly Asn Arg Pro
        50                  55                  60

CTA TTT GAA GAT ATG ACT GAT TCT GAC TGT AGA GAT AAT GCA CCC CGG         417
Leu Phe Glu Asp Met Thr Asp Ser Asp Cys Arg Asp Asn Ala Pro Arg
65                  70                  75                  80

ACC ATA TTT ATT ATA AGT ATG TAT AAA GAT AGC CAG CCT AGA GGT ATG         465
Thr Ile Phe Ile Ile Ser Met Tyr Lys Asp Ser Gln Pro Arg Gly Met
                85                  90                  95

GCT GTA ACT ATC TCT GTG AAG TGT GAG AAA ATT TCA AYT CTC TCC TGT         513
Ala Val Thr Ile Ser Val Lys Cys Glu Lys Ile Ser Xaa Leu Ser Cys
                100                 105                 110

GAG AAC AAA ATT ATT TCC TTT AAG GAA ATG AAT CCT CCT GAT AAC ATC         561
Glu Asn Lys Ile Ile Ser Phe Lys Glu Met Asn Pro Pro Asp Asn Ile
            115                 120                 125

AAG GAT ACA AAA AGT GAC ATC ATA TTC TTT CAG AGA AGT GTC CCA GGA         609
Lys Asp Thr Lys Ser Asp Ile Ile Phe Phe Gln Arg Ser Val Pro Gly
        130                 135                 140
```

```
CAT GAT AAT AAG ATG CAA TTT GAA TCT TCA TCA TAC GAA GGA TAC TTT      657
His Asp Asn Lys Met Gln Phe Glu Ser Ser Ser Tyr Glu Gly Tyr Phe
145                 150                 155                 160

CTA GCT TGT GAA AAA GAG AGA GAC CTT TTT AAA CTC ATT TTG AAA AAA      705
Leu Ala Cys Glu Lys Glu Arg Asp Leu Phe Lys Leu Ile Leu Lys Lys
                165                 170                 175

GAG GAT GAA TTG GGG GAT AGA TCT ATA ATG TTC ACT GTT CAA AAC GAA      753
Glu Asp Glu Leu Gly Asp Arg Ser Ile Met Phe Thr Val Gln Asn Glu
            180                 185                 190

GAC TAGCTA TTAAAATTTC ATGCCGGGCG CAGTGGCTCA CGCCTGTAAT CCCAGCCCTT    812
Asp

TGGGAGGCTG AGGCGGGCAG ATCACCAGAG GTCAGGTGTT CAAGACCAGC CTGACCAACA    872

TGGTGAAACC TCATCTCTAC TAAAAATACT AAAAATTAGC TGAGTGTAGT GACGCATGCC    932

CTCAATCCCA GCTACTCAAG AGGCTGAGGC AGGAGAATCA CTTGCACTCC GGAGGTAGAG    992

GTTGTGGTGA GCCGAGATTG CACCATTGCG CTCTAGCCTG GGCAACAACA GCAAAACTCC   1052

ATCTCAAAAA ATAAAATAAA TAAATAAACA AATAAAAAAT TCATAATGTG AAAAAAAAAA   1112

AAAAAAAA                                                            1120
```

(2) INFORMATION FOR SEQ ID NO:7:

(i) SEQUENCE CHARACTERISTICS:
        (A) LENGTH:10 amino acids
        (B) TYPE:amino acid
        (C) STRANDEDNESS:single
        (D) TOPOLOGY:linear (ii) MOLECULE TYPE:peptide (v) FRAGMENT TYPE:N-terminal fragment (xi) SEQUENCE DESCRIPTION:SEQ ID NO:7:

```
Tyr Phe Gly Lys Leu Glu Ser Lys Leu Ser
1               5                   10
```

(2) INFORMATION FOR SEQ ID NO:8:

(i) SEQUENCE CHARACTERISTICS:
        (A) LENGTH:157 amino acids
        (B) TYPE:amino acid
        (C) STRANDEDNESS:single
        (D) TOPOLOGY:linear (ii) MOLECULE TYPE:peptide (xi) SEQUENCE DESCRIPTION:SEQ ID NO:8:

```
Asn Phe Gly Arg Leu His Cys Thr Thr Ala Val Ile Arg Asn Ile Asn
1               5                   10                  15

Asp Gln Val Leu Phe Val Asp Lys Arg Gln Pro Val Phe Glu Asp Met
                20                  25                  30

Thr Asp Ile Asp Gln Ser Ala Ser Glu Pro Gln Thr Arg Leu Ile Ile
            35                  40                  45

Tyr Met Tyr Lys Asp Ser Glu Val Arg Gly Leu Ala Val Thr Leu Ser
    50                  55                  60

Val Lys Asp Ser Lys Xaa Ser Thr Leu Ser Cys Lys Asn Lys Ile Ile
65                  70                  75                  80

Ser Phe Glu Glu Met Asp Pro Pro Glu Asn Ile Asp Asp Ile Gln Ser
                85                  90                  95

Asp Leu Ile Phe Phe Gln Lys Arg Val Pro Gly His Asn Lys Met Glu
                100                 105                 110
```

```
Phe Glu Ser Ser Leu Tyr Glu Gly His Phe Leu Ala Cys Gln Lys Glu
            115                 120                 125

Asp Asp Ala Phe Lys Leu Ile Leu Lys Lys Asp Glu Asn Gly Asp
        130                 135                 140

Lys Ser Val Met Phe Thr Leu Thr Asn Leu His Gln Ser
145                 150                 155
```

(2) INFORMATION FOR SEQ ID NO:9:

(i) SEQUENCE CHARACTERISTICS:
        (A) LENGTH:193 amino acids
        (B) TYPE:amino acid
        (C) STRANDEDNESS:single
        (D) TOPOLOGY:linear (ii) MOLECULE TYPE:peptide (xi) SEQUENCE DESCRIPTION:SEQ ID NO:9:

```
Met Ala Ala Glu Pro Val Glu Asp Asn Cys Ile Asn Phe Val Ala Met
1               5                   10                  15

Lys Phe Ile Asp Asn Thr Leu Tyr Phe Ile Ala Glu Asp Asp Glu Asn
            20                  25                  30

Leu Glu Ser Asp Tyr Phe Gly Lys Leu Glu Ser Lys Leu Ser Val Ile
        35                  40                  45

Arg Asn Leu Asn Asp Gln Val Leu Phe Ile Asp Gln Gly Asn Arg Pro
50                  55                  60

Leu Phe Glu Asp Met Thr Asp Ser Asp Cys Arg Asp Asn Ala Pro Arg
65                  70                  75                  80

Thr Ile Phe Ile Ile Ser Met Tyr Lys Asp Ser Gln Pro Arg Gly Met
                85                  90                  95

Ala Val Thr Ile Ser Val Lys Cys Glu Lys Ile Ser Xaa Leu Ser Cys
            100                 105                 110

Glu Asn Lys Ile Ile Ser Phe Lys Glu Met Asn Pro Pro Asp Asn Ile
        115                 120                 125

Lys Asp Thr Lys Ser Asp Ile Ile Phe Phe Gln Arg Ser Val Pro Gly
        130                 135                 140

His Asp Asn Lys Met Gln Phe Glu Ser Ser Ser Tyr Glu Gly Tyr Phe
145                 150                 155                 160

Leu Ala Cys Glu Lys Glu Arg Asp Leu Phe Lys Leu Ile Leu Lys Lys
                165                 170                 175

Glu Asp Glu Leu Gly Asp Arg Ser Ile Met Phe Thr Val Gln Asn Glu
            180                 185                 190

Asp
```

(2) INFORMATION FOR SEQ ID NO:10:

(i) SEQUENCE CHARACTERISTICS:
        (A) LENGTH:20 base pairs
        (B) TYPE:nucleic acid
        (C) STRANDEDNESS:single
        (D) TOPOLOGY:linear (xi) SEQUENCE DESCRIPTION:SEQ ID NO:10:

ATRTCRTCDA TRTTYTCNGG                                                      20

(2) INFORMATION FOR SEQ ID NO:11:

(i) SEQUENCE CHARACTERISTICS:
        (A) LENGTH:20 base pairs

```
            (B) TYPE:nucleic acid
            (C) STRANDEDNESS:single
            (D) TOPOLOGY:linear (xi) SEQUENCE DESCRIPTION:SEQ ID NO:11:

TTYGARGAYA TGACNGAYAT                                                    20

(2) INFORMATION FOR SEQ ID NO:12:

(i) SEQUENCE CHARACTERISTICS:
            (A) LENGTH:17 base pairs
            (B) TYPE:nucleic acid
            (C) STRANDEDNESS:single
            (D) TOPOLOGY:linear (xi) SEQUENCE DESCRIPTION:SEQ ID NO:12:

TTYGARGARA TGGAYCC                                                       17

(2) INFORMATION FOR SEQ ID NO:13:

(i) SEQUENCE CHARACTERISTICS:
            (A) LENGTH:26 base pairs
            (B) TYPE:nucleic acid
            (C) STRANDEDNESS:single
            (D) TOPOLOGY:linear (xi) SEQUENCE DESCRIPTION:SEQ ID NO:13:

CGAGGGATCC TACTTTGGCA AGCTTG                                             26

(2) INFORMATION FOR SEQ ID NO:14:

(i) SEQUENCE CHARACTERISTICS:
            (A) LENGTH:26 base pairs
            (B) TYPE:nucleic acid
            (C) STRANDEDNESS:single
            (D) TOPOLOGY:linear (xi) SEQUENCE DESCRIPTION:SEQ ID NO:14:

CAAGGAATTC CTAGTCTTCG GTTTTG                                             26
```

HUMAN INTERFERON-γ INDUCING FACTOR

This is a division of copending parent application Ser. No. 08/558,191 filed Nov. 15, 1995.

BACKGROUND OF THE INVENTION

1. Field of the Invention

The present invention relates to a novel polypeptide which induces the interferon-γ (hereinafter abbreviated as "IFN-γ") production by immunocompetent cells.

2. Description of the Prior Art

It has been said that IFN-γ is a protein which has antiviral-, antioncotic- and immunoregulatory-activities, and is produced by immunocompetent cells stimulated with antigens or mitogens. Because of these biological activities, IFN-γ has been expected for use as an antitumor agent from the beginning of the finding, and studied energetically on clinical trials as a therapeutic agent for malignant tumors in general including brain tumors. IFN-γ preparations now commercially available are roughly classified into 2 groups, i.e. natural IFN-γs produced by immunocompetent cells and recombinant IFN-γs produced by transformants prepared by introducing into microorganisms of the species *Escherichia coli* DNAs which encode the natural IFN-γs. In the above clinical trials, either of these IFN-γs is administered to patients as an "exogenous IFN-γ".

Among these IFN-γs, the natural IFN-γs are usually produced by culturing established immunocompetent cells in nutrient culture media supplemented with IFN-γ inducers to form the IFN-γs, and purifying the IFN-γs. It is known that the type of IFN-γ inducers greatly influence on the IFN-γ production yield, the facilitation of the IFN-γ purification, and the safeness of the final products. Generally, mitogens such as concanavalin A (Con A), *Lens culinaris, Phytolacca americana,* endotoxin and lipopolysaccharide are used. These mitogens, however, have problems of their molecular- and quality varieties depending on their origins and purification methods, as well as difficulty of yielding in a desired amount and in a constant IFN-γ inducibility. In addition, most of these mitogens induce unfavorable side effects when administered to living bodies, and some of them even show toxicity, so that it is substantially difficult to induce the IFN-γ production by directly administering such mitogens to living bodies.

SUMMARY OF THE INVENTION

In view of the foregoing, the object of the present invention is to provide a novel polypeptide which induces the IFN-γ production by immunocompetent cells.

It is another object of the present invention to provide a DNA encoding the polypeptide.

It is further object of the present invention to provide a replicable recombinant DNA which contains the DNA and a self-replicable vector.

It is yet another object of the present invention to provide a transformant obtainable by introducing the recombinant DNA into an appropriate host.

It is another object of the present invention to provide a process for preparing the polypeptide by using the transformant.

[Means to Attain the Object]

The first object of the present invention is attained by a polypeptide which has the amino acid sequence in SEQ ID NO:1 or a homologous amino acid sequence thereunto.

The second object of the present invention is attained by a DNA which encodes the polypeptide.

The third object of the present invention is attained by a replicable recombinant DNA which contains the DNA and a self-replicable vector.

The fourth object of the present invention is attained by a transformant obtainable by introducing the replicable recombinant DNA into an appropriate host.

The fifth object of the present invention is attained by a process for preparing the protein comprising introducing the recombinant DNA into a host, culturing the transformant in a nutrient culture medium, and collecting the formed protein from the resultant culture.

BRIEF DESCRIPTION OF THE ACCOMPANYING DRAWINGS

Figure 1:
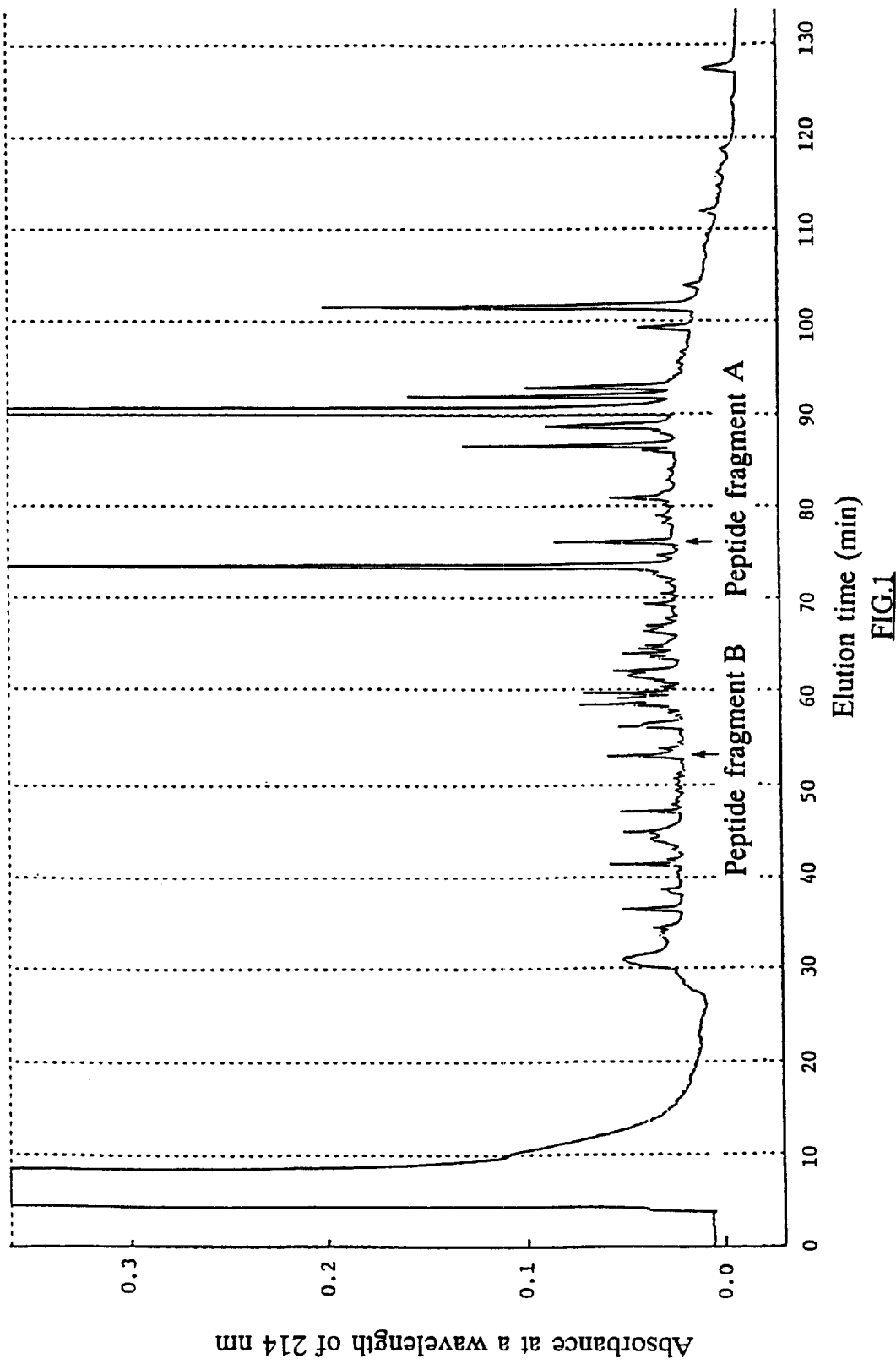
FIG. 1 is an HPLC elution pattern of a peptide fragment obtained by trypsinizing a protein derived from mouse liver.

HIGIF cDNA: cDNA which encodes the present polypeptide

Ptac: tac promoter

GST: glutathione S transferase gene

AmpR: ampicillin resistant gene pBR322ori: replication initiation site of *Escherichia coli*

DETAILED DESCRIPTION OF THE INVENTION

As is described above, the polypeptide according to the present invention has an amino acid sequence which differs from those of conventional polypeptides, and induces the IFN-γ production when allowed alone or together with a cofactor to act on immunocompetent cells.

The DNA according to the present invention expresses the production of the present polypeptide by introducing the DNA into a self-replicable vector to form a recombinant DNA, and, usually, introducing the recombinant DNA into a host capable of proliferating without difficulty but incapable of producing the present polypeptide.

Generally, the replicable recombinant DNA according to the present invention expresses the production of the present polypeptide by introducing it into a host capable of proliferating without difficulty but incapable of producing the present polypeptide.

The transformant produces the polypeptide when cultured.

The present polypeptide is readily obtained in a desired amount by culturing the transformant according to the present process.

The present invention is based on the finding of a novel polypeptide which induces the IFN-γ production by immunocompetent cells. During the study on cytokines produced from mammalian cells, the present inventors found the there exists in mouse liver a novel protein capable of inducing the IFN-γ production. They isolated the protein by using two or more purification methods comprising column chromatography as a main technique and determined for partial amino acid sequence. Based on the above partial amino acid sequence, they chemically synthesized a primer by using as a template a mRNA isolated from mouse liver cells, and treated the protein with transcription-polymerase chain reaction (RT-PCR) in the presence of the primer to collect DNA fragments which partially encode the protein. By using the DNA fragments as a probe, they energetically studied a cDNA library which was alternatively prepared from the mRNA to obtain a DNA fragment consisting of 471 base pairs and having the base sequence of SEQ ID NO:3. The decoding of the base sequence revealed that the protein isolated from mouse liver consists of 157 amino acids and has an amino acid sequence in SEQ ID NO:8, where the symbol "Xaa" means "methionine" or "threonine".

Based on these findings, the present inventors further studied the mRNA derived from human liver cells, and have found that there exists a new gene which encodes a polypeptide which induces the IFN-γ production by immunocompetent cells. The gene contains the base sequence in SEQ ID NO:2, and the decoding thereof revealed that it encodes a polypeptide which consists of 157 amino acids and has the amino acid sequence in SEQ ID NO:1 where the symbol "Xaa" means "isoleucine" or "threonine".

The techniques used to reveal the amino acid sequence and the base sequences in SEQ ID NOs:1 and 2 are summarized in the below:

(1) A protein, which induces the IFN-γ production by immunocompetent cells, was isolated from mouse liver cells and highly purified by combining conventional purification methods comprising chromatography as a main technique;

(2) The resultant purified protein was digested with trypsin, and 2 polypeptide fragments were isolated from the resultant mixture and determined for amino acid sequence;

(3) From mouse liver cells, a mRNA was collected and subjected as a template to the reverse transcription-polymerase chain reaction (RT-PCR) to obtain DNA fragments in the presence of an oligonucleotide as a primer, which had been chemically synthesized based on the above partial amino acid sequence. The DNA fragments were screened by using an oligonucleotide as a probe which had been chemically synthesized based on these partial amino acid sequences, followed by collecting a DNA fragment which partially encodes the protein;

(4) A cDNA library was labeled and hybridized with the resultant cDNA library prepared with the mRNA as a template, followed by selecting a transformant which exhibited a strong hybridization;

(5) A cDNA was isolated from the transformant, and the base sequence was determined and decoded. The comparison of the decoded amino acid sequence and the partial amino acid sequence revealed that the protein has the amino acid sequence in SEQ ID NO:8, and, in mice, the base sequence in SEQ ID NO:3 encodes the amino acid sequence;

(6) A DNA fragment having the base sequence in SEQ ID NO:3 was prepared, labeled and hybridized with a cDNA library which had been prepared by using as a template mRNA derived from human liver cells, followed by selecting a transformant which exhibited a strong hybridization; and (7) The cDNA was prepared from the transformant, determined for base sequence and decoded, revealing that the present polypeptide includes those with the amino acid sequence in SEQ ID NO:1 which is encoded by the base sequence in SEQ ID NO:2 in human.

Through a long term research, the present inventors have found the present polypeptide which induces the IFN-γ production by immunocompetent cells, and, as is evident from SEQ ID NO:1, which differs from conventionally known polypeptides. The present polypeptide includes natural and recombinant polypeptides as long as they have the amino acid sequence in SEQ ID NO:1 or homologous ones thereunto. Variants, which have homologous amino acid sequences to the one in SEQ ID NO:1, can be obtained by replacing one or more amino acids in SEQ ID NO:1 with other amino acids without alternating the inherent biological activity of the present polypeptide. Depending on hosts into which DNAs, even when used the same DNAs, are introduced and on the components and the conditions of cultivation temperature and pH for transformants containing the DNA, it may be formed variants which lack one or more amino acids near to the N- and/or C-termini in SEQ ID NO:1, or additionally contain one or more amino acids near to the N-termini in SEQ ID NO:1 through the modification of internal enzymes of the hosts after the DNA expression, while keeping the inherent biological properties of the polypeptide. The present polypeptide includes such variants as long as they induce the IFN-γ production by immunocompetent cells.

The present polypeptide can be prepared by culturing in nutrient culture media transformants which contain DNAs encoding the polypeptide, and collecting the formed polypeptide from the resultant cultures. The transformants usable in the present invention can be obtained by, for example, introducing into hosts DNAs having the base sequence in SEQ ID NO:2, homologous base sequences thereunto, and complementary ones to these base sequences. One or more bases in those base sequences can be replaced with other bases by means of the degeneracy of genetic code without alternating the amino acid sequence of the present polypeptide. To express the production of the polypeptide in hosts by using such DNAs, one or more bases in base sequences which encode the present polypeptide or its variants can be replaced with other bases.

Any DNA can be used in the present invention as long as it has one of those base sequences independently of their origin, i.e. those from natural sources or artificially synthesized ones. The natural sources include, for example, human liver cells from which the gene, containing the DNA with the base sequence in SEQ ID NO:6, is obtainable. The preparation procedure is as follows: Fractionate a commercially available human liver mRNA supplemented with poly(A) on sucrose gradient buffer to isolate the purified mRNA. Allow a reverse transcriptase and a polymerase to act on the mRNA as a template to form double-stranded cDNA, introduce the cDNA into an appropriate self-replicable vector, and introduce the resultant recombinant DNA into an appropriate host such as *Escherichia coli*. Culture the resultant transformant in a nutrient culture medium, and collect the proliferated transformants containing the DNA encoding the present polypeptide by the colony hybridization method. The DNA according to the present invention is obtainable by treating the transformants with conventional methods. To artificially produce the present DNA, for example, it is prepared by the chemical synthesis based on the base sequence in SEQ ID NO:2, or by introducing a DNA which encodes the amino acid sequence in SEQ ID NO:1 into an appropriate vector to form a recombinant DNA, introducing the recombinant DNA into an appropriate host, culturing the resultant transformant in a nutrient culture medium, isolating the proliferated cells from the culture, and collecting plasmids containing the objective DNA from the cells.

Generally, the DNA was introduced into hosts in the form of a recombinant DNA. Such a recombinant DNA usually contains the DNA and a self-replicable vector, and it can be readily prepared by recombinant DNA technology in general if only the DNA is in hand. Examples of such self-replicable vector are plasmid vectors such as pKK223-2, pGEX-2T, pRL-λ, pBTrp2 DNA, pUB110, YEp13, Ti plasmid, Ri plasmid and pBI121. Among these vectors, pKK223-2, pGEX-2T, pRL-λ, pBTrp2 DNA, pUB110 and YEp13 are suitably used when the present DNA is expressed in procaryotes such as yeasts and other microorganisms of the species *Escherichia coli* and *Bacillus subtilis*, while Ti plasmid, Ri plasmid and pBI121 are suitably used for the expression in animal and plant cells.

To introduce the present DNA into these vectors, conventional methods used in this field can be arbitrarily used: Genes containing the present DNA and self-replicable vectors are cleaved with restriction enzymes and/or ultrasonic, and the resultant DNA fragments and vector fragments are ligated. To cleave genes and vectors, the use of restriction enzymes, which specifically act on nucleotides, more particularly, type II restriction enzymes such as Sau 3AI, Eco RI, Hind III, Bam HI, Sal I, Xba I, Sac I and Pst I, facilitates the ligation of DNA fragments and vector fragments. To ligate DNA fragments and vector fragments, they are, if necessary, first annealed, then treated with a DNA ligase in vivo or in vitro. The recombinant DNAs thus obtained can be readily introduced into appropriate hosts, and this enables the limitless replication of the DNAs by culturing the transformants.

The recombinant DNAs usable in the present invention can be introduced into appropriate hosts such as yeasts and other microorganisms of the species *Escherichia coli* and *Bacillus subtilis:* When microorganisms of the species *Escherichia coli* are used as a host, they are cultured in the presence of the recombinant DNAs and calcium ions, and the competent cell method and the protoplast method are used when microorganisms of the species *Bacillus subtilis* are used as a host. To clone the objective transformants, they are selected by the colony hybridization method or by culturing all the transformants in nutrient culture media, and selecting those which produce polypeptides capable of inducing the IFN-γ production by immunocompetent cells.

The transformants thus obtained produce the present polypeptide intracellularly or extracellularly when cultured in nutrient culture media. Examples of such nutrient culture media are those in the form of liquid in general which contain carbon sources, nitrogen sources and minerals, as well as amino acids and/or vitamins as a micronutrient. The carbon sources usable in the present invention include saccharides such as starch, starch hydrolysates, glucose, fructose and sucrose. The nitrogen sources usable in the present invention include nitrogen containing organic- and inorganic-compounds such as ammonia and their salts, urea, nitrates, peptone, yeast extract, defatted soy bean, corn steep liquor, and beef extract. Transformants are inoculated into nutrient culture media and incubated at a temperature of 25–65° C. and at a pH of 5–8 for about 1–10 days under aerobic conditions by the agitation-aeration method, etc., to obtain cultures containing the present polypeptide. Although the cultures can be used intact as an IFN-γ inducer, they are, if necessary, subjected to ultrasonication and/or cell lysis enzymes to disrupt cells, followed by filtering or centrifuging the resultant suspensions to remove intact cells and cell debris, and further purifying the resultant supernatants containing the present polypeptide. The purification methods usable in the present invention are, for example, those which are generally used in this field to purify biologically active substances, i.e. concentration, salting out, dialysis, separatory sedimentation, gel filtration chromatography, ion-exchange chromatography, hydrophobic chromatography, affinity chromatography, chromatofocusing, gel electrophoresis, and isoelectrophoresis, and, if necessary, two or more of them can be used in combination. The resultant purified solutions containing the present polypeptide can be concentrated and/or lyophilized into liquids or solids to meet to final uses.

As is described above, the present polypeptide has an activity of inducing IFN-γ production by immunocompetent cells. Because of this, the present polypeptide can be arbitrarily used as therapeutic and/or prophylactic agents, for example, those for virus diseases such as AIDS and condyloma acuminatum; malignant tumors such as renal cancer, granuloma, mycosis fungoides and cerebral tumor; and immune disorders such as articular rheumatism and allergy.

The present polypeptide is allowed to coexist in nutrient culture media to induce the IFN-γ production by immunocompetent cells, or directly administered to mammals for the treatment and/or the prevention of IFN-γ susceptive diseases. In the former, leukocytes separated from peripheral blood of mammals, or established immunocompetent cells such as HBL-38 cells, Mo cells, Jurkat cells, HuT78 cells, EL4 cells and L12-R4 cells are suspended in nutrient culture media containing about 0.1 ng to about one μg per ml, preferably, about 1–100 ng per ml of the present polypeptide to induce the IFN-γ production. If necessary, such nutrient culture media can be supplemented with T-cell stimulants such as mitogen, interleukin 2, and anti-CD 3 antibody, and the cells are cultured at a temperature of about 30–40° C. and at a pH of about 5–8 for about 1–100 hours while the media were replacing with fresh ones. IFN-γ can be obtained from the resultant cultures by one or more conventional methods generally used for purifying biologically active substances, for example, concentration, salting out, dialysis, separatory sedimentation, gel filtration chromatography, ion-exchange chromatography, chromatofocusing, gel electrophoresis, and isoelectrophoresis.

To treat and/or prevent IFN-γ susceptive diseases, the present IFN-γ inducing agent is directly administered to mammals: For example, IFN-γ inducing agents are orally administered to mammals after formulated into appropriate forms, or injected to the mammals intradermally, subcutaneously, muscularly, intravenously and peritoneally. The mammals, which can be administered with the present polypeptide, are not restricted to human, and include other animals such as mouse, rat, hamster, rabbit, dog, cat, caw, horse, coat, sheep, pig and monkey. Since the present polypeptide has a strong IFN-γ inducibility and an extremely-low toxicity, it readily induces the IFN-γ production with only a small amount without causing serious side effects even when administered to the mammals in a relatively-high dose. Thus, the present polypeptide advantageously induces a desired amount of IFN-γ smoothly without strictly controlling the dose level. It goes without saying that the present polypeptide fulfills the safeness required for as a pharmaceutical.

The present invention will be explained with reference to the following Examples, and the techniques used therein are in themselves conventionally known in the art: For example, those disclosed by J. Sumbrook et al. in *"Molecular Cloning, A Laboratory Manual"*, 2nd edition (1989), published by Cold Spring Harbor Laboratory Press, New York, USA, and by Masami MURAMATSU in *"Laboratory Manual for Genetic Engineering"* (1988), published by Maruzen Co., Ltd., Tokyo, Japan.

EXAMPLE 1

Preparation of purified polypeptide

To 600 female CD-1 mice, 8-week-old, was intraperitonealy injected one mg/mouse of dead *Corynebacterium*

*parvum* (ATCC 11827) which had been preheated at 60° C. for one hour, and the mice were fed in usual manner for 7 days and intravenously injected with one μg/mouse of a purified lipopolysaccharide derived from *Escherichia coli*. On 1–2 hours after the intravenous injection, the mice were sacrificed to collect their blood, followed by removing their livers, disrupting the livers with a homogenizer in 8-fold volumes of 50 mM phosphate buffer (pH 7.3), and extracting the resultant suspension. The resultant extract was centrifuged at about 8,000 rpm for 20 min, and an about 9 L of the supernatant was admixed with a saturated ammonium sulfate in 50 mM phosphate buffer (pH 7.3) to give a saturation degree of 45 w/v %. The resultant solution was allowed to stand at 4° C. for 18 hours and centrifuged at about 8,000 rpm for 30 min to obtain an about 19 L supernatant containing the present polypeptide.

The supernatant was fed to a column packed with about 4.6 L of "PHENYL SEPHAROSE", a product of Pharmacia LKB Biotechnology AB, Uppsala Sweden, which had been equilibrated with 50 mM phosphate buffer (pH 7.3) containing one M ammonium sulfate, and the column was washed with a fresh preparation of the same buffer, and fed at an SV (space velocity) 0.57 with a linear gradient buffer ranging from 1 M to 0.2 M ammonium sulfate in 50 mM phosphate buffer (pH 7.3). Fractions containing the present polypeptide eluted at 0.8 M ammonium sulfate were collected and pooled into an about 4.8 L solution which was then concentrated with a membrane filter, dialyzed against 20 mM phosphate buffer (pH 6.5) at 4° C. for 18 hours, and fed to a column packed with about 250 ml of "DEAE-SEPHAROSE", a product of Pharmacia LKB Biotechnology AB, Uppsala, Sweden. The column was washed with a fresh preparation of the same buffer and fed at an SV 1.2 with a linear gradient buffer ranging from 0 M to 0.2 M sodium chloride in 20 mM phosphate buffer (pH 6.5) to elute and collect about 260 ml fractions containing the present polypeptide eluted at a concentration of about 0.13 M sodium chloride.

Fractions containing the present polypeptide were collected, pooled, concentrated and dialyzed against 25 mM Bis-Tris buffer (pH 7.1) at 4° C. for 18 hours. The dialyzed solution was applied to a column packed with about 24 ml of "MONO-P", a product of Pharmacia LKB Biotechnology AB, Uppsala, Sweden, and eluted with 10 v/v % polybuffer 74 (pH 4.0) while decreasing the pH from 7 to 4 to obtain an about 23 ml eluate containing the present polypeptide. The eluate was concentrated, fed to a column packed with "SUPER-DEX 75", a product of Pharmacia LKB Biotechnology AB, Uppsala, Sweden, which had been equilibrated with a mixture solution (pH 7.2) containing 7 mM disodium hydrogen phosphate, 3 mM sodium dihydrogen phosphate, and 139 mM sodium chloride, and subjected to gel filtration chromatography to elute fractions, containing the present polypeptide at around 19,000 daltons, with a fresh preparation of the same solution. The fractions were pooled and concentrated for use in Example 2. The yield of the present polypeptide was about 0.6 μg/mouse.

EXAMPLE 2

Partial amino acid sequence

A portion of an aqueous solution containing the purified polypeptide in Example 1 was concentrated up to a volume of about 50 μl which was then admixed with 25 μl of a solution containing 3 w/v % SDS, 60 v/v % glycerol, and 60 mg/ml dithiothreitol. The resultant mixture was incubated at 50° C. for 30 min, positioned on 15 w/v % polyacrylamide gel, and electrophoresed in usual manner. The resultant gel was stained by soaking it in a mixture solution of 10 v/v % aqueous acetic acid solution and 50 v/v % aqueous methanol containing 0.1 w/v % coomassie brilliant blue R 250, destained by repeatedly washing the gel with a mixture Solution of 12 v/v % aqueous methanol and 7 v/v % aqueous acetic acid solution, and washed by soaking it in distilled water for 18 hours. A portion of the gel, which was stained with the coomassie brilliant blue and contained the present polypeptide, was cut out of the gel, and lyophilized.

The lyophilized gel was soaked i n 0.6 ml solution consisting of 100 mM sodium hydrogen carbonate containing 2 μg/ml "TPCK TRYPSIN", 0.5 mM calcium chloride, and 0.02 v/v % aqueous Tween 20 solution, followed by the incubation at 37° C. for 18 hours to trypsinize the protein. The resultant was centrifuged to obtain a supernatant, while the resultant precipitate was soaked in one ml of one v/v % aqueous trifluoroacetate containing 0.001 v/v % Tween 20, shook for 4 hours at ambient temperature, and centrifuged to obtain a supernatant. The newly formed precipitate was successively treated similarly as above with 70 v/v aqueous trifluoroacetate containing 0.001 v/v Tween 20 and with 50 v/v % aqueous acetonitrile to obtain a supernatant. The resultant supernatant and the already obtained supernatant in the above were pooled and concentrated up to give 250 μl which was then centrifugally filtered.

The resultant aqueous solution containing peptide fragments was fed to "HPLC ODS-120T", a column for HPLC commercialized by Tosoh Corporation, Tokyo, Japan, which had been previously equilibrated with 0.1 v/v aqueous trifluoroacetate, and the column was washed with 0.1 v/v % aqueous trifluoroacetate, and fed with 0.1 v/v % trifluoroacetate at a flow rate of 0.5 ml/min while the concentration of aqueous acetonitrile was increasing from 0 v/v % to 70 v/v % and the concentration of peptide in the eluate was monitoring by a spectrophotometer at wave lengths of 214 nm and 280 nm. Fractions eluted about 75 min and about 55 min after initiating the elution were respectively collected (hereinafter named "peptide fragment A" and "peptide fragment B"). The elution pattern was in FIG. 1.

The peptide fragments A and B were analyzed on "MODEL 473 A", a protein sequencer commercialized by Perkin-Elmer Corp., Instrument Div., Norwalk, USA, and revealed that they have the amino acid sequences in SEQ ID NOs:4 and 5.

EXAMPLE 3

Base sequence of DNA encoding protein and amino acid sequence of protein

EXAMPLE 3-1

Preparation of whole RNA

Three g of wet mouse liver cells, similarly prepared by the method in Example 1, was weighed, soaked in 20 ml of a mixture solution containing 6 M guanidine isothiocyanate, 10 mM sodium citrate, and 0.5 w/v SDS, and disrupted with a homogenizer. Thirty-five-ml centrifugation tubes were injected with 25 ml of 0.1 M EDTA (pH 7.5) containing 5.7 M cesium chloride, and 10 ml of the homogenized cell suspension was overlaid on the upper part of the solutions in the tubes, followed by centrifuging the tubes at 25,000 rpm for 20 hours to collect RNA fractions. The fractions were pooled, distributed into 15-ml centrifugation tubes, and mixed with equal volumes of a mixture solution of chloroform and isobutanol (=4:1 by volume). The tubes were vibrated for 5 min and centrifuged at 4° C. and at 10,000 rpm for 10 min, and the formed water layers were collected, pooled, mixed with 2.5-fold volumes of ethanol, and allowed to stand at −20° C. for 2 hours to precipitate the whole RNAs. The precipitate was collected, pooled, washed with 75 v/v % aqueous ethanol, and dissolved in 0.5 ml of sterilized distilled water for use in Experiment 3-2. The yield of the RNAs was about 4 mg, on a dry solid basis (d.s.b.).

EXAMPLE 3-2

Preparation of DNA fragments encoding partially the present polypeptide

One μg of the whole RNAs in Example 3-1 was mixed with 4 μl of 25 mM magnesium chloride, 2 μl of a solution of 10×PCR buffer consisting of 100 mM Tris-HCl buffer (pH 8.3) and 500 mM potassium chloride, 8 μl of one mM dNTP mix, one μl of a solution containing one unit/μl RNase inhibitor, one μl of a solution containing 2.5 units/μl reverse transcriptase, and one μl of 2.5 μM random hexamer, and further mixed with water to give a total volume of 20 μl. The mixture solution was placed in 0.5 ml reaction tubes, and, in usual manner, successively incubated at 25° C. for 10 min, at 42° C. for 30 min, at 99° C. for 5 min, and at 5° C. for 5 min to effect the reverse transcriptase reaction, followed by recovering an aqueous solution containing the first strand cDNA.

To 20 μl of the aqueous solution were added 4 μl of 25 mM magnesium chloride, 8 μl of 10×PCR buffer, 0.5 μl of a solution containing 2.5 units/μl of AmpliTaq DNA polymerase commercialized by Perkin-Elmer Corp., Instrument Div., Norwalk, USA, and one pmole each of primers 1 and 2 as a sense primer or an anti-sense primer. The mixture solution was volumed up to 100 μl with sterilized distilled water, and, in usual manner, successively incubated at 94° C. for one min, at 45° C. for 2 min, at 72° C. for 3 min in a cyclic manner for 40 cycles to amplify a DNA fragment, which partially encodes the present polypeptide, by using the first strand cDNA as a template. The primers 1 and 2 were oligonucleotides, which were chemically synthesized based on the amino acid sequences of Pro-Glu-Asn-Ile-Asp-Asp-Ile (amino acids 10–16 of SEQ ID NO:4) and Phe-Glu-Asp-Met-Thr-Asp-Ile (amino acids 4–10 of SEQ ID NO:5) had the base sequences of 5'-ATRTCRTCDATRTTYTCNGG-3' (SEQ ID NO:10) and 51-TTYGARGAYATGACNGAYAT-3' (SEQ ID NO: 11).

A portion of the resultant PCR product was fractionated on electrophoresis in 2 w/v § agarose gel, transferred on a nylon film, fixed with 0.4 N sodium hydroxide, washed with 2×SSC, air-dried, soaked in a prehybridization solution containing 5×SSPE, 5×Denhard's solution, 0.5 w/v e SDS and 100 μg/ml of denatured salmon sperm DNA, and incubated at 65° C. for 3 hours. An oligonucleotide as a probe 1 having a base sequence of 5'-TTYGARGARATGGAYCC-3' (SEQ ID NO:12) was synthesized based on the amino acid sequence of Phe-Glu-Glu-Met-Asp-Pro (amino acids 4–10 of SEQ ID NO:4), and labeled with [γ-$^{32}$P]ATP and T4 polynucleotide kinase. The nylon film was soaked in a solution containing one pmole of the probe 1, 5×SSPE, 5×Denhardt's solution, 0.5 w/v % SDS, and 100 μg/ml of a denatured salmon sperm DNA, and incubated at 45° C. for 24 hours to effect hybridization. The resultant nylon film was washed with 6×SSC and autoradiographed in usual manner and revealed that the PCR product contained the objective DNA fragment.

The remaining PCR product was mixed with 50 ng of "pT7 BLUE T", a plasmid vector commercialized by Takara Shuzo Co., Ltd., Tokyo, Japan, an adequate amount of T4 ligase, and further mixed with 100 mM ATP up to give a concentration of one mM, followed by the incubation at 16° C. for 18 hours to insert the DNA fragment into the plasmid vector. The recombinant DNA thus obtained was introduced into *Escherichia coli* NoVa Blue strain, a microorganism of the species *Escherichia coli* commercialized by Pharmacia LKB Biotechnology AB, Uppsala, Sweden, to obtain a transformant which was then inoculated into a medium plate containing 10 g/l bactotryptone, 2.5 g/l sodium chloride, 15 g/l bacto-agar, 100 mg/l ampicillin, 40 mg/l X-Gal and 23.8 mg/l isopropyl-β-D-thiogalacto-pyranoside (hereinafter abbreviated as "IPTG"), and incubated at 37° C. for 24 hours to form colonies. A nylon film was in usual manner overlaid on a medium plate and allowed to stand for about 30 seconds to attach the colonies thereunto. The nylon film was then detached from the plate and soaked for 7 min in a solution containing 0.5 N sodium hydroxide and 1.5 M sodium chloride to effect cell lysis. Thereafter, the nylon film was further soaked for 3 min in 0.5 M Tris-HCl buffer (pH 7.2) containing 1.5 M sodium chloride, washed with 2×SSC, soaked in 0.4 N sodium hydroxide for 20 min to fix the DNA, washed with 5×SSC, air-dried, soaked in a prehybridization solution containing 5×SSPE, 5×Denhardt's solution, 0.5 w/v % SDS, and 100 μg/ml denatured salmon sperm DNA, and incubated at 65° C. for 3 hours. The colonies formed on the nylon film were in usual manner hybridized with the probe 1, washed with 6×SSC, and autoradiographed similarly as above, followed by selecting transformants which strongly hybridized with the probe 1.

The transformants were inoculated in L-broth (pH 7.2) containing 100 μg/ml ampicillin and incubated at 37° C. for 18 hours, followed by collecting cells from the culture and collecting recombinant DNA by conventional alkali-SDS method. The analysis of the dideoxy method revealed that the recombinant DNA contained a DNA fragment which consists of base sequences corresponding to those positioning from 85 to 281 in SEQ ID NO:3.

EXAMPLE 3-3

Preparation of mRNA 0.05 ml of an aqueous solution containing the whole RNAs in Example 3-1 was placed in a test tube, admixed with 0.5 ml of 10 mM Tris-HCl buffer (pH 7.5) containing one mM EDTA and 0.1 w/v % SDS, and volumed up to one ml with sterilized distilled water. To the mixture was added one ml "OLIGOTEX-dT30 SUPER", an oligo-d(T)$_{30}$ latex commercialized by Nippon Roche K.K., Tokyo, Japan, followed by the incubation at 65° C. for 5 min to denature the RNAs and the cooling for 3 min in an ice-chilled bath. The resultant mixture was admixed with 0.2 ml of 5 M sodium chloride, incubated at 37° C. for 10 min, and centrifuged at 10,000 rpm at 25° C. for 10 min. The precipitate in the form of a pellet was suspended in 0.5 ml sterilized distilled water, and incubated at 65° C. for 5 min to extract mRNA from the oligo-d(T)$_{30}$ latex. The yield of the mRNA was about 5 μg.

EXAMPLE 3-4

Preparation of cDNA library cDNA Library was prepared from the mRNA in Example 3-3 by using "cDNA SYNTHESIZING SYSTEM PLUS", a cDNA cloning kit commercialized by Amersham Corp., Div., Amersham International, Arlington Heights, USA. The procedures were as follows: To 1.5-ml reaction tube were successively added 4 μl of a solution for synthesizing the first strand cDNA, one μl sodium pyrophosphate solution, one μl of a solution of human placenta ribonuclease inhibitor, 2 μl deoxynucloside triphosphate mix, and one μl oligo-d(T)$_{16}$ primer. The resultant mixture was mixed with 2 μl of mRNA in Experiment 3-3, volumed up to 19 μl with sterilized distilled water, mixed with one μl of a solution containing 20 units of reverse transcriptase, and incubated at 42° C. for 40 min to obtain a reaction mixture containing the first strand cDNA.

The mixture thus obtained was mixed with 37.5 μl of a solution for synthesizing the second strand cDNA, 0.8 units of ribonuclease H derived from *Escherichia coli*, 23 units of DNA polymerase, and volumed up to 100 μl with sterilized distilled water. The resultant mixture was successively incubated at 12° C. for 60 min and at 22° C. for 60 min, mixed with 2 units of T4 DNA polymerase, and incubated at 37° C. for 10 min to obtain a reaction mixture containing the second strand cDNA. To the reaction mixture was added 4 μl of 0.25 M EDTA (pH 8.0) to suspend the reaction, and the resultant mixture was in usual manner extracted with phenol and chloroform and treated with ethanol to precipitate the objective cDNA, followed by recovering the precipitate.

To the cDNA thus obtained were added 2 μl of L/K buffer, 250 pmole Eco RI adaptor, and 2.5 units of T4 DNA ligase in this order, and the resultant solution was volumed up to 20 μl with sterilized distilled water, and incubated at 15° C. for 16 hours to ligate the Eco RI adaptor to the both ends of the cDNA. The reaction mixture was mixed with 2 μl of 0.25 M EDTA to inactivate the remaining enzyme, and subjected to molecular sieve chromatography to remove intact Eco RI adaptor. To the resultant were added 40 μl of LIK buffer, 80 units of T4 polynucleotide kinase, and the mixture was volumed up to 400 μl with sterilized distilled water, followed by the incubation at 37° C. for 30 min to methylate the Eco RI cleavage sites. The resultant mixture was extracted with phenol and chloroform and treated with ethanol to precipitate the objective DNA, followed by recovering the DNA. To the DNA were added 1.5 μl of L/K buffer containing an adequate amount of λgt 10 arms, and 2.5 units of T4 DNA ligase, and the resultant solution was volumed up to 15 μl with sterilized distilled water, incubated at 15° C. for 16 hours to effect ligation, and subjected to conventional in vitro packaging method to obtain a phage containing a recombinant λDNA.

EXAMPLE 3-5
Cloning of recombinant DNA

A seed culture of *Escherichia coli* NM514 strain was in usual manner infected with the phage in Example 3-4, and the infected cells were inoculated in an agar plate (pH 7.0) containing 10 g/l bacto-tryptone, 5 g/l bacto-yeast extract, 10 g/l sodium chloride and 15 g/l bacto-agar, and incubated at 37° C. for 16 hours to form plaques. The agar plate was covered with a nylon film and allowed to stand for about 30 seconds to attach the plaques thereunto. The nylon film was detached from the plate, and successively soaked in an aqueous solution containing 0.5 M sodium hydroxide and 1.5 M sodium chloride for 7 min and in 0.5 M Tris-HCl buffer (pH 7.0) containing 1.5 M sodium chloride for 3 min. The nylon film was washed with 2×SSC, air-dried, soaked in 0.4 N sodium hydroxide for 20 min, washed with 5×SSC, air-dried, soaked in a solution containing 5×SSPE, 5×Denhardt's solution, 0.5 w/v % SDS, and 100 μg/ml denatured salmon sperm DNA, and incubated at 65° C. for 3 hours. Thereafter, the resultant nylon film was incubated in a solution containing an adequate amount of DNA fragment as the probe 2 obtained in Example 3-2 and labeled with $^{32}P$ by "READY PRIME DNA LABELLING SYSTEM", a DNA labeling kit commercialized by Amersham Corp., Div., Amersham International, Arlington Heights, USA, 5×SSPE, 5×Denhardt's solution, 0.5 w/v D SDS, and 100 μg/ml of denatured salmon sperm DNA, and the mixture was incubated at 60° C. for 20 hours to effect hybridization. The resultant was subjected to radioautography similarly as above to select phage DNA clones which strongly hybridized with the probe 2.

With conventional techniques, the clones were amplified in *Escherichia coli*, followed by extracting a recombinant DNA from the cells. The recombinant DNA was cleaved with Eco RI, a restriction enzyme. Plasmid vector pUC19 ($ATCC_{37254}$) was cleaved with the same restriction enzyme, and the resultant cleaved DNA fragments and plasmid fragments were ligated with DNA ligase to obtain a recombinant DNA which was then introduced into *Escherichia coli* JM109 strain ($ATCC_{53323}$) by conventional competent cell method to obtain a transformant.

EXAMPLE 3-6
Determination of base sequence of DNA and amino acid sequence of protein The transformant in Example 3-5 was inoculated into L-broth (pH 7.2) and cultured at 37° C. for 18 hours under shaking conditions. The resultant proliferated cells were collected and treated with conventional alkali-SDS method to obtain a recombinant DNA containing the DNA according to the present invention. The analysis on an automatic sequencer using a fluorophotometer revealed that the recombinant DNA contains the base sequence from the 5'-terminus in SEQ ID NO:3. The decoding of the base sequence indicated that it encodes the amino acid sequence containing the N-terminus in SEQ ID NO:8. The amino acid sequence contains the partial amino acid sequences in SEQ ID NOs:4 and 5 corresponding to those positioning from 79 to 103 and from 26 to 43 in SEQ ID NO:8, and this means that the present polypeptide contains the amino acid sequence containing the N-terminus in SEQ ID NO:8, and that it is encoded by a DNA containing the base sequence from the 5'-terminus in SEQ ID NO:8 where the symbol "Xaa" means "methionine" or "threonine".

In the following Examples 4 to 7, a cDNA, which encodes another polypeptide that induces the IFN-γ production by immunocompetent cells, is prepared from human liver mRNA by using as a probe a DNA fragment of the base sequence in SEQ ID NO:3. The cDNA was analyzed for base sequence and decoded to determine the amino acid sequence of the polypeptide. The cDNA was allowed to express in *Escherichia coli*, followed by studying the feature and property of the formed polypeptide.

EXAMPLE 4
Base sequence of DNA encoding polypeptide and amino acid sequence of polypeptide

EXAMPLE 4-1
Preparation of cDNA library cDNA library was prepared from a human liver RNA supplemented with "POLY A", a product commercialized by Clonatec-BIOSOFT, Paris Cedex, France, by using "cDNA SYNTHESIZING SYSTEM PLUS", a cDNA cloning kit commercialized by Amersham Corp., Div., Amersham International, Arlington Heights, USA. The procedures were as follows: To 1.5-ml reaction tube were successively added 10 μl of a solution for synthesizing the first strand cDNA, 2.5 μl of one mM sodium pyrophosphate, 2.5 μl of a solution containing one μg/l of a human placenta ribonuclease inhibitor, 5 μl of a solution containing one μg/l of a deoxynucleotide triphosphate mix, 2.5 μl of a solution containing one μg/l oligo-dT primer, 5 μl of a human liver RNA supplemented with poly(A), and volumed up to 45 μl with sterilized distilled water. Thereafter, the resultant mixture was mixed with 5 μl of a solution containing a reverse transcriptase, and incubated at 42° C. for 40 min to obtain a reaction mixture containing the first strand cDNA.

To the reaction mixture was added 93.5 μl of a solution for synthesizing the second strand cDNA, 4 units of ribonuclease H derived from *Escherichia coli*, 115 units of DNA polymerase, and volumed up to 250 µl with sterilized distilled water. The resultant mixture was successively incubated at 12° C. for 60 min, at 22° C. for 60 min, and at 70° C. for 10 min, mixed with 10 units of T4 polymerase, and further incubated at 37° C. for 10 min. To the reaction mixture was added 10 µl of 0.25 M EDTA (pH 8.0) to suspend the reaction, and the resultant mixture was in usual manner extracted with phenol and chloroform, and treated with ethanol to precipitate the objective second strand cDNA, followed by recovering the precipitate.

To the second strand cDNA thus obtained were added 2 µl L/K buffer (pH 8.0), 250 pmole Eco RI adaptor, and 2.5 units of T4 DNA ligase, and the resultant solution was volumed up to 20 µl with sterilized distilled water, and incubated at 15° C. for 16 hours to ligate the Eco RI adaptor to the both ends of the cDNA. The resultant mixture was then mixed with 2 µl of 0.25 M EDTA to suspend the reaction, and subjected to molecular sieve chromatography to remove intact Eco RI adaptor. To the resultant were added 40 µl of L/K buffer (pH 8.0) and 80 units of T4 polynucleotide kinase, and the mixture was volumed up to 400 µl with sterilized distilled water, followed by the incubation at 37° C. for 30 min to methylate the Eco RI cleavage sites. The resultant mixture was extracted with phenol and chloroform and treated with ethanol to precipitate the objective cDNA, followed by recovering the cDNA. To the cDNA were added 1.5 µl of L/K buffer (pH 8.0) containing an adequate amount of λgt 10 arms, and 2.5 units of T4 DNA ligase, and the resultant solution was volumed up to 15 µl with sterilized distilled water, incubated at 15° C. for 16 hours to effect ligation, and subjected to conventional in vitro packaging method to obtain a phage containing a recombinant λDNA.

EXAMPLE 4-2

Cloning of recombinant DNA

A seed culture of *Escherichia coli* NM514 strain was in usual manner infected with the phage in Example 4-1, and the infected cells were inoculated in an agar plate (pH 7.0) containing 10 g/l bacto-trypton, 5 g/l bacto-yeast extract, 10 g/l sodium chloride, and 15 g/l bacto-agar, and incubated at 37° C. for 16 hours to form plaques. According to conventional method, the agar plate was covered with a nylon film and allowed to stand for about 30 seconds to attach the plaques thereunto. Thereafter, the nylon film was detached from the plate, and successively soaked in an aqueous solution containing 0.5 N sodium hydroxide and 1.5 M sodium chloride for 7 min and in 0.5 M Tris-HCl buffer (pH 7.0) containing 1.5 M sodium chloride for 3 min. The nylon film was washed with 2×SSC, air-dried, soaked in 0.4 N sodium hydroxide for 20 min, washed with 5×SSC, air-dried, soaked in a solution containing 5×SSPE, 5×Denhardt's solution, 0.5 w/v % SDS and denatured salmon sperm DNA, and incubated at 65° C. for 3 hours. To clone the objective recombinant DNA, a DNA fragment having the base sequence in SEQ ID NO:3 was labeled with 32p by "READY PRIME DNA LABELLING SYSTEM", a DNA labeling kit commercialized by Amersham Corp., Div., Amersham International, Arlington Heights, USA, to obtain probe 3. The procedures were as follows: Place in 1.5-ml reaction tube 25 ng of a DNA fragment prepared by the method in Example 3–5, volumed up to 45 µl of sterilized distilled water, incubated at 95° C. for 3 min, and transferred to another reaction tube. Five µl of [α-$^{32}$P]dCTP solution was added to the reaction tube, and labeled by incubating it at 37° C. for 30 min. Thereafter, the resultant product containing the labeled DNA fragment was subjected to conventional molecular sieve chromatography to remove intact [α-$^{32}$P].

The above nylon film was soaked in a mixture solution containing 5×SSPE, 5×Denhardt's solution, 0.5 w/v % SDS, and 100 µg/ml of a denatured salmon sperm DNA, and the mixture was incubated at 60° C. for 20 hours to effect hybridization, and further incubated at ambient temperature in 6×SSC for 20 min and in 2×SSC for 20 min. The resultant was washed and subjected to autoradiography similarly as above to select phage DNA clones which strongly hybridized with the probe 3.

With conventional techniques, the DNA clones were amplified in *Escherichia coli*, followed by the extraction of a recombinant DNA from the cells. The recombinant DNA was cleaved with Eco RI, a restriction enzyme. Plasmid vector pUC19 (ATCC 37254) was cleaved with the same restriction enzyme, and the cleaved DNA fragments and plasmid fragments were ligated with DNA ligase to obtain a recombinant DNA which was then introduced into *Escherichia coli* JM109 strain (ATCC$_{53323}$) by conventional competent cell method to obtain a transformant containing the present DNA.

EXAMPLE 4-3

Determination of base sequence and amino acid sequence

The transformant in Example 4-2 was inoculated into L-broth (pH 7.2) containing 50 µg/ml of ampicillin, and cultured at 37° C. for 18 hours under shaking conditions. The proliferated cells were collected by centrifugation and treated with conventional alkali-SDS method to extract a recombinant DNA. The analysis of the base sequence on an automatic sequencer using a fluorophotometer revealed that the recombinant DNA contains the base sequence in SEQ ID NO:9. The amino acid sequence estimable from the base sequence is also shown in SEQ ID NO:9, and this indicates that the present polypeptide has an amino acid sequence, for example, the one in SEQ ID NO:1, and that the polypeptide is encoded by the DNA of the base sequence in SEQ ID NO:2. In SEQ ID NO:6, the amino acid as shown by "Xaa" means "isoleucine" or "threonine".

EXAMPLE 5

Preparation of replicable recombinant DNA and transformant

To a 0.5-ml reaction tube were added 8 µl of 25 mM magnesium chloride, 10 µl of 10×PCR buffer, 8 µl of one mM dNTP mix, 0.5 µl of a solution containing 2.5 units/µl AmpliTaq DNA polymerase, and one ng of the recombinant DNA in Example 4-2. The resultant mixture was mixed with adequate amounts of 2 oligonucleotides, as a sequence primer or anti-sense primer, having base sequences represented by 5,-CGAGGGATCCTACTTTGGCAAGCTTG-3' (SEQ ID NO:13) and 5'-CAAGGAATTCCTAGTCTTCGTTTTG-3' (SEQ ID NO:1) which had been chemically synthesized based on the base sequences near to the N- and C-termini in SEQ ID NO:1, and volumed up to 100 µl with sterilized distilled water. The resultant mixture was in usual manner successively incubated at 94° C. for one min, at 60° C. for 2 min, and at 72° C. for 3 min, and this incubation cycle was repeated for 40 times to obtain a PCR product which was then cleaved with Bam HI and Eco RI as restriction enzymes to obtain a Bam HI-Eco RI DNA fragment. The resultant Bam HI-Eco RI DNA fragment was mixed with an adequate amount of sterilized distilled water. The solution was mixed with 10 ng "pGEX-2T", a plasmid vector commercialized by Pharmacia LKB Biotechnology AB, Uppsala, Sweden, which had been previously cleaved with Bam HI and Eco RI as a restriction enzyme, 10 µl of 10×ligation buffer, and an adequate amount of 10 mM ATP to give a final concentration of one mM, followed by the incubation at 16° C. for 18 hours to obtain the replicable recombinant DNA pHIGIF.

Figure 2:
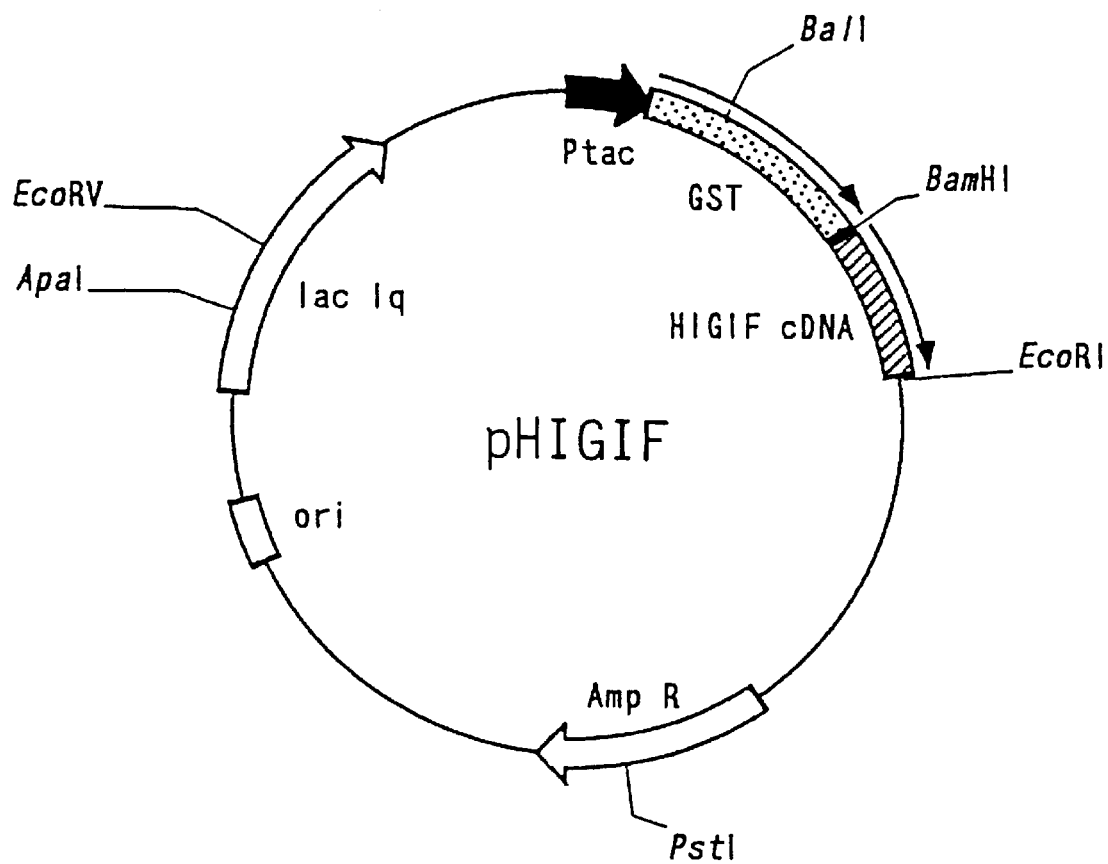
FIG. 2 is a figure of the structure of the present recombinant DNA pHIGIF.

The recombinant DNA pHIGIF was introduced into *Escherichia coli* DH5α strain commercialized by Toyobo Co., Ltd., Tokyo, Japan, and the resultant transformant "HIGIF" was inoculated into L-broth (pH 7.2) containing 50 μg/ml ampicillin, and incubated at 37° C. for 18 hours under shaking conditions. The resultant culture was centrifuged to obtain the proliferated transformants which were then subjected to conventional alkali-SDS method to extract the recombinant DNA pHIGIF. The analysis of the recombinant pHIGIF on the dideoxy method revealed that as shown in FIG. 2 "HIGIF cDNA" or the cDNA in SEQ ID NO:2 ligated to the sites in the downstream of genes for Tac promotor and glutathione S-transferase.

EXAMPLE 6
Production of polypeptide from transformant

The transformant HIGIF in Example 5 was inoculated into T-broth (pH 7.2) containing 50 μg/ml of ampicillin, and incubated at 37° C. for 18 hours under shaking conditions to obtain a seed culture. Eighteen L aliquots of a fresh preparation of T-broth (pH 7.2) were placed in 30-L jar fermenters, inoculated with one v/v % of the seed culture, and cultured at 37° C. under aeration-agitation conditions. During the cultivation, the culture was sampled and monitored for absorbance at a wave length of 650 nm, and, when the absorbance reached to about 1.5, IPTG was added to the culture up to give 0.1 mM. Thereafter, the culture was further incubated for another 5 hours and centrifuged to separate cells from the culture. The cells were suspended in a mixture solution (pH 7.2) containing 139 mM sodium chloride. 7 mM disodium hydrogen phosphate, and 3 mM sodium dihydrogen phosphate, treated in usual manner with ultrasonic, and centrifuged to obtain a supernatant.

The supernatant was fed to a column packed with "GLUTATHIONE SEPHAROSE 4B", a product of Pharmacia LKB Biotechnology AB, Uppsala, Sweden, which had been previously equilibrated with a mixture solution (pH 7.2) containing 139 mM sodium chloride, 7 mM disodium hydrogen phosphate and 3 mM sodium dihydrogen phosphate. The column was washed with a fresh preparation of the same mixture solution, and 100 U of thrombin was added to one ml of the gel in the column to effect enzymatic cleavage reaction while allowing the column to stand at ambient temperature for 16 hours. The column was fed with a fresh preparation of the same mixture solution to elute the reaction product, and the eluate was fed to a column packed with "SUPERDEX 75", a product of Pharmacia LKB Biotechnology AB, Uppsala, Sweden, followed by collecting fractions corresponding near to 18,500 daltons. The fractions were pooled, concentrated and lyophilized to obtain a solid product containing the present polypeptide in a yield of about 80 μg per one L of the culture.

EXAMPLE 7
Physicochemical property of polypeptide

EXAMPLE 7-1
Molecular weight

In accordance with the method reported by U. K. Laemmli in *Nature*, Vol.227, pp.680–685 (1970), the purified polypeptide prepared by the method in Example 6 was electrophoresed in a sodium dodecyl sulfate (SDS) polyacrylamide gel free of reducing agent to mainly show a single protein band with an IFN-γ inducibility at a position corresponding to about 18,500±3,000 daltons. The marker proteins used in this experiment were calf serum albumin (MW=67,000 daltons), ovalbumin (MW=45,000 daltons), soy bean trypsin inhibitor (MW=20,100 daltons), and α-lactalbumin (MW=14,400 daltons).

EXPERIMENT 7-2
Isoelectric point

The purified polypeptide in Example 6 was chromatofocused to show an isoelectric point of about 4.9±1.0.

EXAMPLE 7-3
Amino acid sequence containing the N-terminus

The purified polypeptide in Example 6 was analyzed on "MODEL 473 A", a protein sequencer commercialized by Perkin-Elmer Corp., Instrument Div., Norwalk, USA, and revealed that it has the structure wherein a peptide, "Gly-Ser-", coupled to the tyrosine residue in the N-terminal amino acid sequence in SEQ ID NO:7 by the addition of glutathione S-transferase and by the cleavage with thrombin.

EXAMPLE 7-4
Biological activity

From female C3H/HeJ mice, 8-week-old, were extracted their spleens which were then suspended in serum-free RPMI 1640 medium (pH 7.4), and the resultant cells were washed with a fresh preparation of the same medium, and soaked in Gey solution (pH 8.0) to effect hemolysis. The resultant spleen cells were suspended in RPMI 1640 medium (pH 7.4) supplemented with 10 v/v % calf serum to give a cell density of $1\times10^7$ cells/ml. Ten ml aliquots of the cell suspension were distributed into plastic petri dishes, 9 cm in diameter, and incubated at 37° C. for one hour in a 5 v/v % $CO_2$ incubator. Only cells floating in the resultant cultures were collected and washed with RPMI 1640 medium (pH 7.4) supplemented with 10 v/v % calf serum for use in the following test for IFN-γ induction.

Mouse spleen cells were suspended in RPMI 1640 medium (pH 7.4) supplemented with 10 v/v % calf serum to give a cell density of $1\times10^7$ cells/ml, and 0.15 ml aliquots of which were injected into 96-well microplates, followed by adding to each well 0.05 ml of a solution of a purified polypeptide diluted with a fresh preparation of the same medium, and incubating the cells with or without the addition of 0.05 ml of 2.5 μg/ml of concanavalin A or 50 units/ml of interleukin 2, and incubating the resultant at 37° C. for 24 hours in a 5 v/v % $CO_2$ incubator. After completion of the culture, the resultant supernatant in each well was sampled by 0.1 ml to assay the activity of the formed IFN-γ with enzyme immunoassay. As a control, a system similar to the above system was provided and similarly treated as above except for not using the purified polypeptide, concanavalin A and interleukin 2. As an IFN-γ standard, a mouse IFN-γ preparation Gg02-901-533, obtained from the National Institutes of Health, USA, was used and the activity was expressed with international units (IU). The results were in Table 1.

TABLE 1

| | IFN-γ production by mouse spleen cell (IU/ml) | | |
| --- | --- | --- | --- |
| Sample concentration (μg/ml) | Sample | Sample plus concanavalin A | Sample plus interleukin 2 |
| 10.00 | 12 | 138 | 118 |
| 3.33 | 6 | 88 | 55 |
| 1.11 | 5 | 56 | 16 |
| 0.37 | 5 | 21 | 12 |
| 0.12 | 5 | 12 | 10 |

TABLE 1-continued

| | IFN-γ production by mouse spleen cell (IU/ml) | | |
|---|---|---|---|
| Sample concentration (µg/ml) | Sample | Sample plus concanavalin A | Sample plus interleukin 2 |
| 0.04 | 5 | 11 | 7 |
| 0 | 0 | 4 | 1 |

Note: In the Table "Sample" means the present polypeptide.

EXAMPLE 7-4(b)
Induction of IFN-γ production from human lymphocyte

By using a syringe containing heparin, a healthy donor was collected blood which was then diluted by 2-fold with serum-free RPMI 1640 medium (pH 7.4), and overlaid on ficoll. The resultant was centrifuged at 2,000 rpm for 20 min to obtain lymphocytes which were then washed with RPMI 1640 medium (pH 7.4) supplemented with 10 v/v % calf serum, suspended in a fresh preparation of the same medium to give a cell density of 5×10⁶ cells/ml, and treated similarly as in Example 7-4(a) except that a human IFN-γ standard, Gg23-901-530, obtained from the National Institutes of Health, USA, was used as an IFN-γ standard. The results were in Table 2.

TABLE 2

| | IFN-γ production by human lymphocyte (IU/ml) | | |
|---|---|---|---|
| Sample concentration (µg/ml) | Sample | Sample plus concanavalin A | Sample plus interleukin 2 |
| 10.00 | 191 | 479 | 1,182 |
| 3.33 | 169 | 576 | 1,419 |
| 1.11 | 168 | 426 | 1,106 |
| 0.37 | 150 | 296 | 739 |
| 0.12 | 74 | 193 | 390 |
| 0.04 | 36 | 137 | 324 |
| 0 | 1 | 11 | 24 |

Note: In the Table "Sample" means the present polypeptide.

The results in Tables 1 and 2 evidence that the present polypeptide has an activity of inducing IFN-γ production by immunocompetent cells of mammals including human and mouse. In the control groups, any significant IFN-γ production was not found, while in the systems with the polypeptide a significant IFN-γ production was observed. This activity of the polypeptide is strongly augmented when used in combination with concanavalin A or interleukin 2 as a cofactor.

The present invention is based on the finding of a novel polypeptide which induces the IFN-γ production by immunocompetent cells. The polypeptide is a substance which has a partially or totally revealed amino acid sequence, and a stable activity of inducing IFN-γ production by immunocompetent cells. Therefore, the present polypeptide is widely used as an IFN-γ inducer for the IFN-γ production by the cell culture method and as a therapeutic and/or prophylactic agent in general for IFN-γ susceptive diseases such as viral diseases, malignant tumors, and immunopathies.

The present polypeptide has a strong IFN-γ inducibility so that it can induce a desired amount of IFN-γ production with only a relatively small amount. The polypeptide dose not cause serious side effects even when administered to in a relatively-high dose because it only has an extremely-low toxicity. Therefore, the present polypeptide has an advantage that it promptly induces a desired amount of IFN-γ production without strictly controlling the dose.

The present polypeptide with such an usefulness can be readily prepared in a desired amount by using DNAs which encode the polypeptide.

Thus, the present invention is a significant invention which has a remarkable effect and gives a great contribution to this field.

While there has been described what is at present considered to be the preferred embodiments of the invention, it will be understood the various modifications may be made therein, and it is intended to cover in the appended claims all such modifications as fall within the true spirit and scope of the invention.

We claim:

1. An isolated DNA molecule comprising a nucleotide sequence which encodes a polypeptide comprising an amino acid sequence selected from the group consisting of:
   (a) SEQ ID NO:1,
   (b) a contiguous fragment of SEQ ID NO:1, and
   (c) a variant of (a) or (b) differing therefrom by the replacement of one amino acid residue;
   wherein a polypeptide consisting of said amino acid sequence.

2. A replicable recombinant DNA molecule comprising the nucleotide sequences of a self-replicable vector and a DNA molecule according to claim 1.

3. The replicable DNA molecule according to claim 2, which comprises the nucleotide sequence of SEQ ID NO:6.

4. The replicable recombinant DNA molecule according to claim 2, wherein said vector is a plasmid vector.

5. A host cell transformed with the replicable recombinant DNA molecule according to claim 2.

6. The transformed host cell according to claim 5, wherein the replicable recombinant DNA molecule comprises the nucleotide sequence of SEQ ID NO:6.

7. The transformed host cell according to claim 5, wherein said vector of said replicable recombinant DNA molecule is a plasmid vector.

8. The transformed host cell according to claim 5, wherein said host is a microorganism of the species *Escherichia coli*.

9. A process for preparing a human interferon-γ inducing factor comprising the steps of:
   (a) culturing in a nutrient culture medium the transformed host cell according to claim 5 to produce a human interferon-γ inducing factor; and
   (b) collecting the produced human interferon-γ inducing factor from the resultant culture.

10. The process according to claim 9, wherein said vector is a plasmid vector.

11. The process according to claim 9, wherein said host is a microorganism of the species *Escherichia coli*.

12. The process according to claim 9, wherein the human interferon-γ inducing factor produced is purified by one or more techniques selected from the group consisting of concentrating, salting out, dialysis, separatory sedimentation, gel filtration chromatography, affinity chromatography, chromatofocusing, gel electrophoresis, and isoelectric point electrophoresis.

13. The isolated DNA molecule of claim 1, wherein said polypeptide encoded by said nucleotide sequence comprises the amino acid sequence of SEQ ID NO:1.

14. The isolated DNA molecule of claim 1, wherein said polypeptide encoded by said nucleotide sequence comprises the amino acid sequence of a contiguous fragment of SEQ ID NO:1.

15. The isolated DNA molecule of claim 1, wherein said polypeptide encoded by said nucleotide sequence comprises a variant of (a) or (b) differing therefrom by the replacement of one amino acid residue.

16. An isolated DNA molecule encoding human interferon-γ inducing factor comprising the nucleotide sequence shown in SEQ ID NO:2.

17. A replicable recombinant DNA molecule comprising the nucleotide sequences of a self-replicable vector and a DNA molecule according to claim 16.

18. A host cell transformed with the replicable recombinant DNA molecule according to claim 17.

19. A process for preparing a human interferon-γ inducing factor, comprising the steps of:
culturing the transformed hosts cell according to claim 18 in a nutrient medium to produce a human interferon-γ inducing factor which induces interferon-γ production by human immunocompetent cells; and
collecting the produced human interferon-γ inducing factor from the resultant culture.

20. An isolated DNA molecule, comprising a nucleotide sequence encoding a polypeptide which induces IFN-γ production by immunocompetent cells and comprises the amino acid sequence of SEQ ID NO:1, where Xaa represents isoleucine or threonine.

21. The isolated DNA molecule according to claim 20, wherein said nucleotide sequence encoding said polypeptide comprises the nucleotide sequence of SEQ ID NO:6.

22. A replicable Recombinant DNA molecule comprising the nucleotide sequences of a self-replicable vector and a DNA molecule according to claim 20.

23. The replicable recombinant DNA molecule according to claim 22, wherein said self-replicable vector is a plasmid.

24. A host cell transformed with the replicable recombinant DNA according to claim 22.

25. The host cell according to claim 24, wherein said host cell is a microorganism of *Escherichia coli*.

26. A process for preparing a human interferon-γ inducing factor, comprising the steps of:
culturing the transformed hosts cell according to claim 24 in a nutrient medium to produce a human interferon-γ inducing factor which induced interferon-γ production by human immunocompetent cells; and
recovering the produced human interferon-γ inducing factor.

27. A purified polypeptide, comprising an amino acid sequence selected from the group consisting of:
(a) SEQ ID NO:1,
(b) a contiguous fragment of SEQ ID NO:1, and
(c) a variant of (a) or (b) differing therefrom by replacement of one amino acid residue;
wherein a polypeptide consisting of said amino acid sequence induces interferon-γ production in immunocompetent human cells.

28. The purified polypeptide of claim 27, which has a molecular weight of about 18,000±3,000 daltons on sodium dodecyl sulfate polyacrylamide gel electrophoresis (SDS-PAGE) and an isoelectric point of about 4.9±1.0 on chromatofocusing.

29. The purified polypeptide of claim 27, which comprises the amino acid sequence of SEQ ID NO:1, where Xaa at residue 73 is isoleucine or threonine.

30. The purified polypeptide of claim 27, which comprises the amino acid sequence of a contiguous fragment of SEQ ID NO:1.

31. The purified polypeptide of claim 27, which comprises a variant of (a) or (b) differing therefrom by replacement of one amino acid residue.

* * * * *